March 15, 1966 | G. JAMES | Plant Pat. 2,607
PECAN TREE
Filed Aug. 24, 1964 | 2 Sheets-Sheet 1
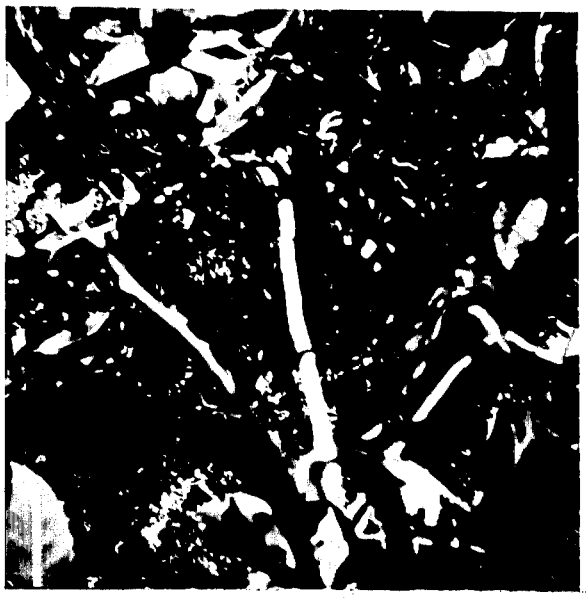
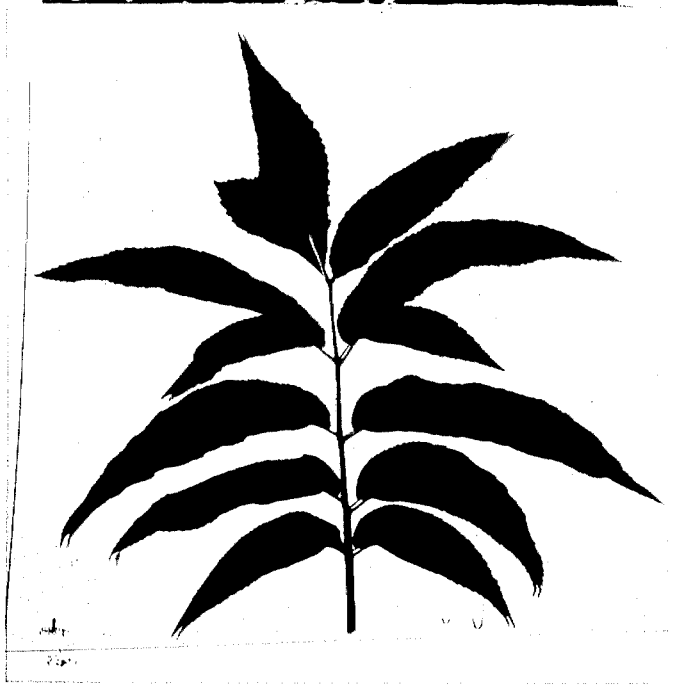
Inventor.
George James
By: Robb & Robb
Attorneys.

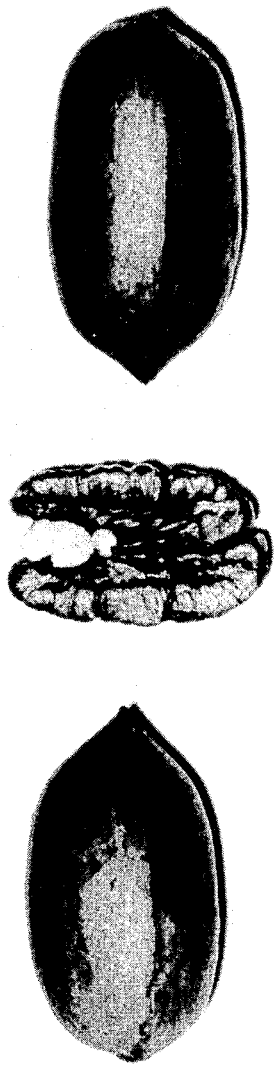
Inventor.
George James
By: Robb & Robb
Attorneys

United States Patent Office

Plant Pat. 2,607
Patented Mar. 15, 1966

2,607
PECAN TREE

George James, % James Pecan Farms, Brunswick, Mo.

Filed Aug. 24, 1964, Ser. No. 391,821
1 Claim. (Cl. Plt.—31)

The present invention relates to a new and distinct variety of pecan tree which was discovered by me as a limb sport originating in my pecan grove on my farm near Brunswick, Chariton County, Missouri.

At the time of my discovery aforementioned, my attention was attracted to one particular tree in the grove referred to above, while in the course of inspecting my cattle which were grazing in said grove which consisted of pecan seedlings of unknown parentage. On this occasion, I noticed a limb on this particular tree which bore leaves of unusually large size and of an exceptionally glossy dark green color, giving the impression of a tropical plant. Continued observations of the original sport and of progeny thereof convinced me that it is a new variety which is distinct from all others of which I am aware, as evidenced by a unique combination of the following characteristics which are outstanding therein:

(1) Dwarfish, but rapid, vigorous and hardy habits of growth;

(2) Exceptional abundance of glossy dark green leaves, giving the appearance of a tropical plant with consequent suitability for use as a lawn or shade tree;

(3) An unusually large size of the leaves; and (4) Abundant production of nuts similar to those of the variety known as the "James Pecan," and distributed in commerce under the trademark "Starking" Hardy Giant, Plant Patent No. 1,361, said nuts being large in size, thin-shelled, so as to crack easily, and well filled with plump kernels of good flavor.

Asexual reproduction of my new pecan variety, as performed by grafting and budding, shows that the foregoing characteristics come true to form and are established and transmitted through succeeding propagations.

The accompanying drawings show a portion of a tree, with nut clusters borne thereby, and a typical specimen of the foliage on an enlarged scale, all as depicted in color, and also showing in black and white typical unshelled and shelled nut specimens which depict the general form and other details thereof.

The following is a detailed description of my new pecan variety, with color terminology in accordance with Ridgway's Color Standards and Nomenclature (hereinafter abbreviated (R)) and Koster's Color Guide (hereinafter abbreviated (K)), as indicated, except where general color terms of ordinary dictionary significance are obvious:

Locality where grown and observed: Near Brunswick, Missouri.

Parentage: A limb sport of a seedling of unknown parentage.

Dates of first and last pickings: Usually picked all at once, about September 23 to September 30.

Propagation: Holds its distinguishing characteristics through succeeding propagations by both budding and grafting.

Maturity season: About September 23 to September 30.

Tree:

*Size.*—Small.

*Productivity.*—Good; regular bearer.

*Growth habit.*—Dwarfish, but extremely vigorous; very hardy.

*Wood.*—Smooth. Limbs—heavy. Twigs—rate of growth averages about 15 inches to 18 inches per year, as compared with 3 to 4 inches in the case of the seedling parent. Color—Wood Drab, Plate XLVI, Color No. 17 (R).

*Foliage.*—Very abundant; very large; very dense. Leaves—usually compound of 13 leaflets, measuring from 18 to 24 inches in length. Leaflets—extremely large, measuring about 9½ inches long and 3 inches wide. Color—very dark green, corresponding to near Taxus Green, Plate 81 (K), with lighter green veins.

*Buds.*—Usually borne close together. Shape—long oval. Color—brown.

Nuts:

*Ripening.*—Even.

*Time of harvesting.*—From about September 23 to September 30.

*Quantity.*—About 75% of nut clusters produce 5 nuts, with about 15% producing 4 nuts, and the remainder producing 2 or 3 nuts.

*Tenacity.*—Free.

*Cluster.*—Open. Size—large.

*Nut size.*—From about 1 inch to 1½ inches long and from about ⅞ inch to 1 inch in diameter.

*Shell thickness.*—Thin.

*Average number of nuts to the pound.*—From about 70 to 74.

*Shape.*—Oblong, with round base and mucronate point.

*Shell.*—Cracks and releases very easily, due to thin shell. Color—similar to that of "James Pecan" (Plant Patent No. 1,361), but with fewer black markings.

*Kernel.*—Color—light brown. Flavor—very good. Shape—plump. Texture vary firm. Sutures even.

Disease and insect resistance. My new pecan variety has shown no evidence of any fungus diseases, and the leaves show less damage by nut case bearer, as compared with other varieties grown in the same area and under the same conditions near Brunswick, Missouri.

I claim:

A new and distinct variety of pecan tree, substantially as herein shown and described, characterized particularly as to novelty by the unique combination of dwarfish, but rapid, vigorous and hardy habits of growth, exceptional abundance of glossy dark green leaves, giving the appearance of a tropical plant with consequent suitability for use as a lawn or shade tree, an unusually large size of the leaves, and abundant production of nuts similar to those of the variety known as the "James Pecan," and distributed in commerce under the trademark "Starking" Hardy Giant, Plant Patent No. 1,361, said nuts being large in size, thin-shelled, so as to crack easily, and well filled with plump kernels of good flavor.

No references cited.

ABRAHAM G. STONE, *Primary Examiner.*